United States Patent
Predescu-Melzer

(10) Patent No.: US 12,128,218 B2
(45) Date of Patent: Oct. 29, 2024

(54) NEEDLELESS EPIDERMAL SYRINGE FOR NEEDLE-FREE INJECTION OF ACTIVE INGREDIENT-CONTAINING SOLUTION

(71) Applicant: Alina Predescu-Melzer, Richterswil (CH)

(72) Inventor: Alina Predescu-Melzer, Richterswil (CH)

( * ) Notice: Subject to any disclaimer, the term of this patent is extended or adjusted under 35 U.S.C. 154(b) by 773 days.

(21) Appl. No.: 17/292,774

(22) PCT Filed: Nov. 11, 2019

(86) PCT No.: PCT/EP2019/080886
§ 371 (c)(1),
(2) Date: May 11, 2021

(87) PCT Pub. No.: WO2020/099331
PCT Pub. Date: May 22, 2020

(65) Prior Publication Data
US 2021/0393880 A1   Dec. 23, 2021

(30) Foreign Application Priority Data

Nov. 12, 2018 (DE) .................... 10 2018 128 273.7

(51) Int. Cl.
*A61M 5/30* (2006.01)
(52) U.S. Cl.
CPC ..................... *A61M 5/30* (2013.01)
(58) Field of Classification Search
CPC ..... A61M 5/30; A61M 5/2046; A61M 5/2053
See application file for complete search history.

(56) References Cited

U.S. PATENT DOCUMENTS

| | | |
|---|---|---|
| 3,688,765 A | 9/1972 | Gasaway |
| 4,940,460 A | 7/1990 | Casey et al. |
| 4,941,880 A | 7/1990 | Burns |

(Continued)

FOREIGN PATENT DOCUMENTS

EP   0295917 A2   12/1988

OTHER PUBLICATIONS

Chu; "Device may inject a variety of drugs without using needles;" MIT News Office; May 24, 2012; https://news.mit.edu/2012/Needleless-injections-0524.

(Continued)

*Primary Examiner* — Theodore J Stigell
(74) *Attorney, Agent, or Firm* — PATENT PORTFOLIO BUILDERS PLLC

(57) ABSTRACT

A needleless epidermal syringe includes an injector housing, a gas cartridge, and a piston that moves under the pressure produced by a release of gas from the gas cartridge. Movement is in particular linearly, inside the injector housing. The pressure can be transmitted by the piston onto an active substance-containing solution, and enables its delivery to the subcutaneous tissue via an administering opening in the needleless epidermal syringe upon placing it on the skin. The needleless epidermal syringe includes a lever element, upon the activation of which the gas cartridge is pressed in order to release gas onto a nozzle included in the injector housing and tapering towards the gas cartridge. This releases gas in order to move the piston when the active substance-containing solution is injected.

11 Claims, 3 Drawing Sheets

(56) References Cited

U.S. PATENT DOCUMENTS

Figure 1:
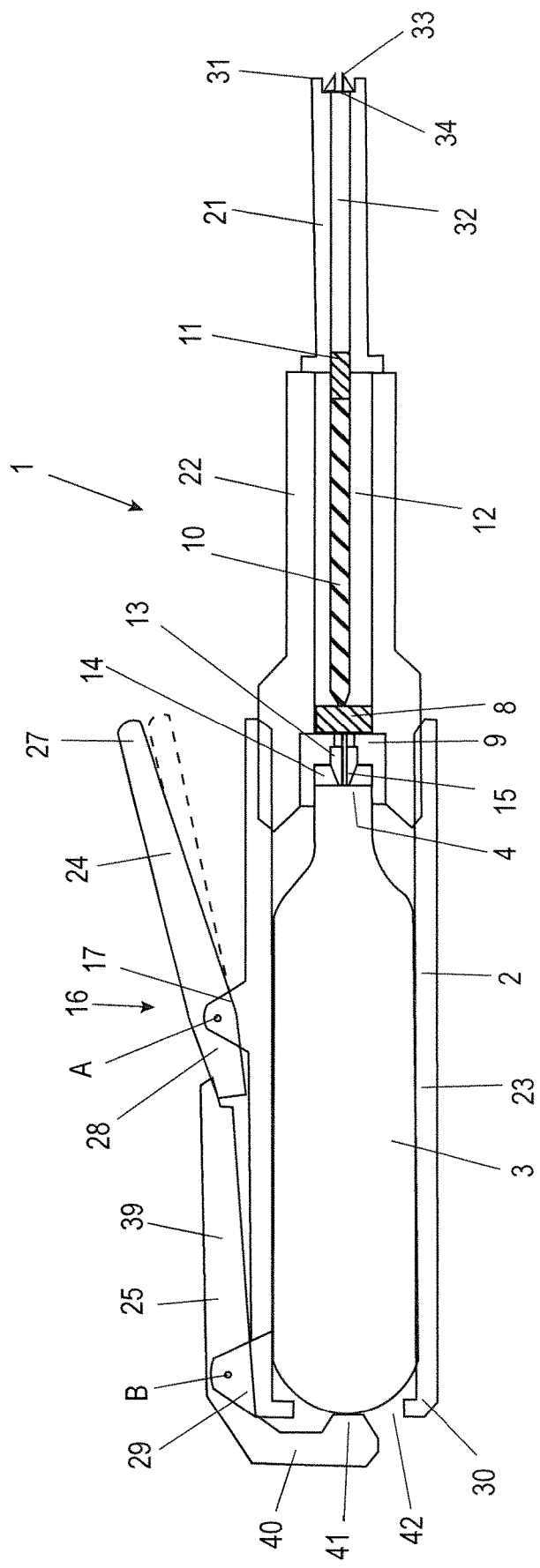

| | | | |
|---|---|---|---|
| 5,899,880 A * | 5/1999 | Bellhouse | C12M 35/00 |
| | | | 222/631 |
| 6,264,629 B1 | 7/2001 | Landau | |
| 6,752,781 B2 * | 6/2004 | Landau | A61M 5/30 |
| | | | 604/209 |
| 2004/0215135 A1 * | 10/2004 | Sheldrake | A61M 5/3015 |
| | | | 604/68 |
| 2014/0361036 A1 | 12/2014 | Brouillette et al. | |

OTHER PUBLICATIONS

International Search Report mailed Feb. 25, 2020 in related/corresponding International Application No. PCT/EP2019/080886.
Search Report created on Jun. 27, 2019 in related/corresponding DE Application No. 10 2018 128 273.7.
Written Opinion mailed Feb. 25, 2020 in related/corresponding International Application No. PCT/EP2019/080886.

* cited by examiner

NEEDLELESS EPIDERMAL SYRINGE FOR NEEDLE-FREE INJECTION OF ACTIVE INGREDIENT-CONTAINING SOLUTION

BACKGROUND AND SUMMARY OF THE INVENTION

Exemplary embodiments of the invention are directed to a needleless epidermal syringe.

Needleless epidermal syringes are known as state of the art. It involves pressure on the active ingredient-containing solution, strong enough to penetrate the surface of the skin tissue.

When choosing how pressure should be applied, various possibilities exist. It can be differentiated between a spring-driven tension mechanism, which exercises spring pressure on a piston, and a pneumatic mechanism, which functions through gas pressure.

One can find on the internet website http://news.mit.edu/2012/Needleless-injections-0524 a description of a magnet activated needleless injection device.

In the area of spring-driven tension mechanism, the injection devices that are already known use a lever to create tension on the spring mechanism. The tensioning of a drive mechanism, however, can be spared in a pneumatic drive, whereas a pressure is already built up, and only needs to be released.

In the U.S. Pat. No. 6,264,629 B1, among others in FIG. 5, an injection device with a pneumatic mechanism is shown. Based on the force lines it can be recognized that the operating pressure is mounted over a cap axial to the device axis.

Such force input from the axial direction would lead to an undesirable excessive axial pressure on the injection device, and thus on the skin and the injection spot. This, for example, could lead, in case of an inflamed spot, to unnecessary pain or inflammation center spread. Furthermore, a considerable amount of pressure must be implemented in order to trigger the gas cartridge. The pressure in the gas cartridge should be relatively high in order to use it, so that the lock fixture, which needs to be smashed first, is rather stable.

Exemplary embodiments are directed to an injection device that is inexpensive to manufacture and easy to use.

A needleless epidermal syringe, according to the invention, is used for a needle-free injection of an active ingredient-containing solution through the skin surface into a lower subcutaneous tissue.

The injection device comprises of an injector housing and a gas cartridge. Furthermore, the injection device has a piston, for example a rod-shaped syringe piston, that becomes movable by pressure of gas release from the gas cartridge, especially in a linear direction, inside the injection housing. For this purpose, the injection housing may contain a channel that serves as the piston guidance. The piston acts on the active ingredient-containing solution, and pushes it into the channel that extends linearly in the direction of movement of the piston in the injection housing.

The pressure is transferred through the piston's movement to the active ingredient-containing solution. The solution is delivered to the subcutaneous tissue by means of the pressure transmission to an exit opening in the needless epidermal syringe when it is placed on the skin.

According to the invention, the needleless epidermal syringe also has a lever element, which, upon activation, presses the gas cartridge and releases gas to a nozzle located inside the injector housing, and pointing towards the gas cartridge.

This allows the gas to move the piston upon injection of the active ingredient-containing solution. The lever element enables a simple and less forced activation of the injection device of the current invention.

The lever element can advantageously be made of two or more parts with a plurality of levers. The lever, in such case, will form part of the lever element.

At least one lever of the lever element is mounted in such a way, that in order to release gas, the lever element presses on the gas cartridge at least in some areas, preferably in a parallel direction to the housing axis of the injector housing.

The lever element, in particular one lever of the lever element, can preferably have two legs which are at such an angle to one another, so that a force is redirected from an activating force in a radial direction to the housing axis C of the injector housing in an axially directed force.

The force redirection does not necessarily have to be 90°. Preferably, the force deviation will be at least 70°, whereas 80 to 100° will be preferred.

The gas cartridge can be filled, so that gas pressure of at least 100 ATM, preferably more than 180 ATM is applicable to the piston.

The needless epidermal syringe may have a channel filled with the active ingredient-containing solution, and the diameter of the discharge opening located at its end should be at least four times, preferably ten times smaller than the diameter of the channel. This allows a further increase in pressure before injection of the solution.

A first lever of at least two levers in the lever element may be located outside the injector housing, e.g., at its outer circumference, with a tilt angle of at least 3°, preferably 5 to 20°, relative to the injector housing. That will enable a lever effect that is large enough for power transmission.

The first lever of the lever element may essentially be of a linear shape, which can be formed as a switch deviating from a tilting axis, whereas a first lever arm should be at least four times, preferably eight times, as long as a second lever arm acting on a second lever.

The second lever of the lever element may have a curved form—especially an L-form, whereas a first lever arm of the second lever, to which the first lever holds, will preferably be twice as large as the second lever, for the application of pressure on the gas cartridge.

The injection device, especially the injector housing, can be constructed of several parts, whereby the respective parts are connected to but can be separated from each other. It may have a pneumatic drive unit with the gas cartridge, and a power transmission unit that transfers the pressure to the solution. The power transmission unit includes the piston that can move in a linear direction inside the injector housing. Ultimately, the injection device may also have a drug chamber with a storing channel that releases the active ingredient-containing solution into the subcutaneous tissue.

The injection element may have a locking mechanism that locks the lever element from being unintentionally used, and its deactivation, e.g., removal, enables a tilting movement of the lever element.

The injector housing and the lever element can be produced of plastic at lower their cost.

Upon activation of the lever element, its force can directly transmitted to the gas cartridge, i.e., no other force-transmitting elements such as springs or the like are involved.

Thanks to its simple design, the possibility of low-cost components' manufacturing and the small number of components, the injection device is suitable for single use.

BRIEF DESCRIPTION OF THE DRAWING FIGURES

Figure 2:
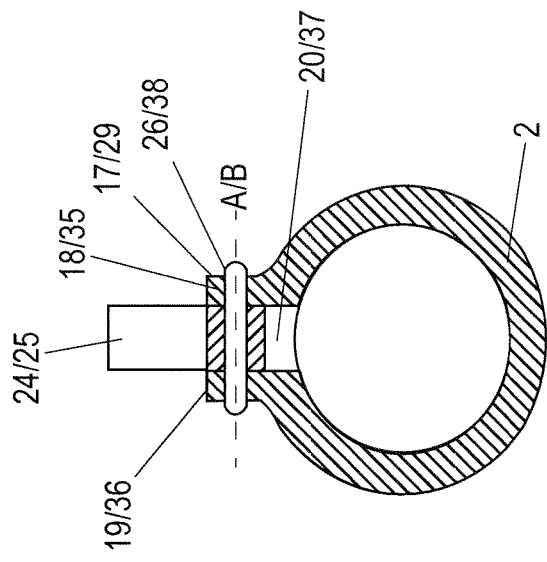
Figure 3:
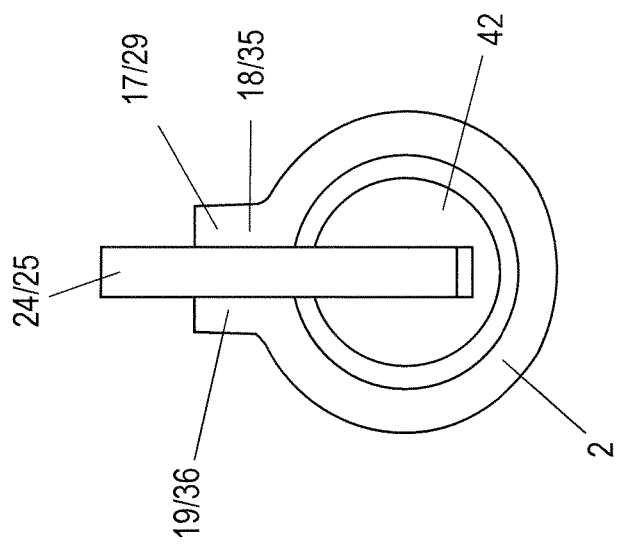
Figure 4:
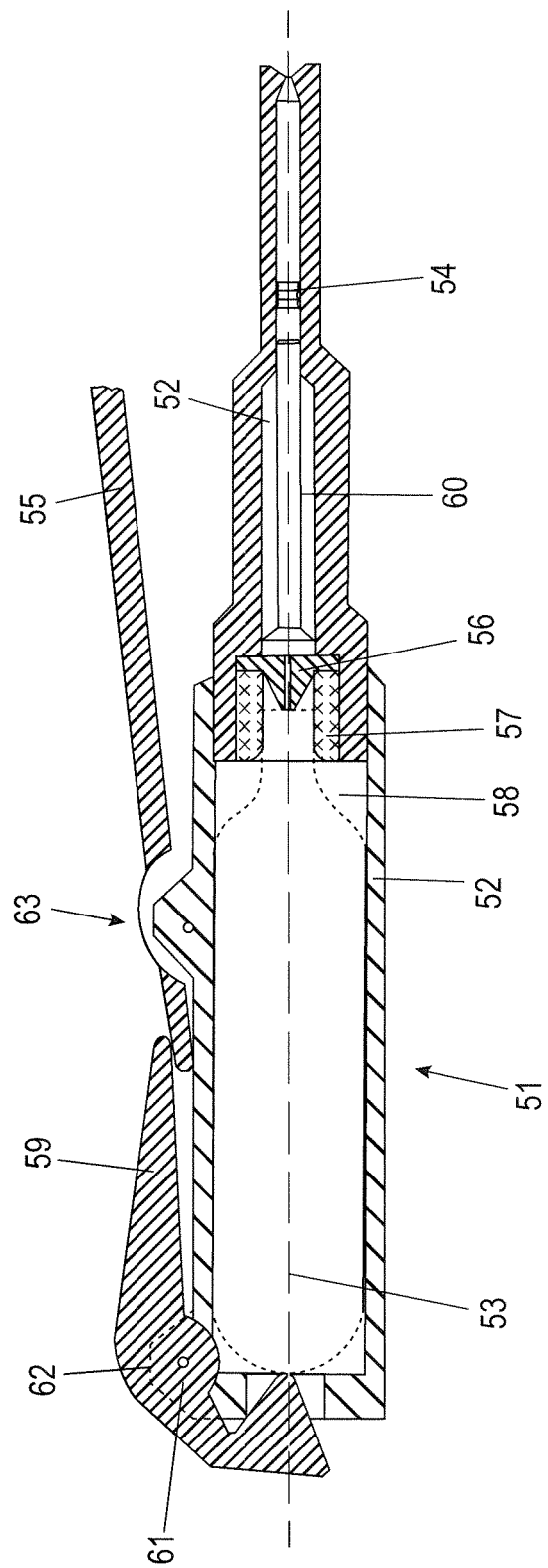

Hereinafter the invention is presented in detail, based on a produced example and the following figures: Shown are:

FIG. 1 schematic sectional view of a first injection device according to the invention;

FIG. 2 Top view of the injection device according to the invention;

FIG. 3 Sectional view of the injection device according to the invention at a pivot axis level of a lever element; and FIG. 4 schematic sectional view of a second injection device according to the invention,

DETAILED DESCRIPTION

FIG. 1-3 show a produced example of injection device 1 according to the invention.

The injection device 1 provides the needle-free injection of an active ingredient-containing solution to a subcutaneous tissue. Injection device 1 has an injector housing 2, which in the case of FIG. 1 can be divided into three injector housing sections 21, 22 and 23. The injection housing sections 21, 22 and 23 can be mounted to each other separately, e.g., by means of a screw.

A first injection housing section 21 has a front surface 31 that is designated for contact with skin. The first injection housing section 21 is shaped as a pencil sleeve. It includes a channel 32 for transmission of the solution to an administering opening 33 for the injection of the solution onto the skin. Channel 32 has, in the area of the administering opening 33, a cross-section reduction 34. The diameter of the cross-sectional reduction 34 is at least twice smaller than the diameter in the remaining area of channel 32, preferably even ten times and smaller than the diameter of channel 32. The cross-section reduction allows to increase pressure additionally, on the delivered solution before it hits the skin.

In its initial status, the solution to be injected may be located within channel 32. The length of channel 32 can be changed according to the solution dosage. This enables the complete filling of the channel and finally covering it with a foil or alike. Anyway, the filling of channel 32 and the build-up of the complete injection device 1 can also be performed on-site by the producer.

In the channel 32 it is possible to insert a rod-shaped syringe piston 10. The syringe piston 10 has a sealing attachment 11 at the end, so that no solution can escape at the edge of the syringe piston 10, whereas such event could lead to a reduction of pressure in the remaining solution in channel 32.

At the interface between the first injector housing section 21 and the adjoining second injector housing section 22, there is a seal, e.g., a sealing ring, through which the rod-shaped syringe piston 10 is guided to move. The second injector housing section has a channel 12 for guiding the rod-shaped syringe piston 10 and a sealing element 8, arranged at the end and firmly connected to the syringe piston 10. Due to the dimensions of the sealing element 8, the channel 12 has a larger diameter than channel 32 of the first injector housing section 21. An insert 9 with a central nozzle 13 is located at the end of the duct 12, the insert 9 allows gas to be introduced into channel 12 and exerts pressure on the sealing element 8, to guide the syringe piston 10 in a linear movement in the direction of the administering opening 33. The nozzle 13 reduces in the opposite direction to the above-mentioned linear movement and forms a tip 14 with a gas inlet opening 15, to allow the destruction of the gas cartridge in the area of a cartridge seal 4 by piercing the seal introducing the released gas into the channel 12.

The third injection housing section has an intake space for the gas cartridge. In the case of FIG. 1, a so called 12 g gas cartridge is used. Gas cartridges 3 have a cartridge cap that can be destroyed mechanically. In the demonstration example of FIG. 1, this might be a cartridge cap that can be punctured. Of course, the cartridge cap should be stable enough, so to withhold the gas pressure within the cartridge. Therefore, in the pneumatic operated injection device a simple use always possible, and it is necessary to exercise considerable force in order to destroy the cartridge cap.

In addition to the components that support force, such as springs and/or caps, the injection device is often structured in a way that prevents its use as a disposable injection device.

The following invention offers, for the activation of the gas cartridge 3, a solution that is significantly simpler and easier to handle, by means of a two-parts lever element 16. The lever element 16 is easily accessible from outside, on the injection housing 2. The lever element comprises of a first, mainly linear, lever 24 and a second L-formed lever 25, that function upon each other.

In order to position the first lever 24, a first lever bearing 17 sticks out from the main cylindrical third injector housing section 23. The lever bearing 17 comprises of two lugs 18, 19 and a gap 20 into which the lever 24 can be inserted at least part by part by means of an axle bolt 26, tiltably arranged in openings in the two lugs 18 and 19. This first lever 24 is also referred to hereinafter as the rocker lever. Axle bolt 26 defines a tilt axis A, around which lever 24 performs a tilting movement. The lever 24 is separated by the tilting axis to a first and a second lever arm 27, 28, whereby the first lever arm 27 is at least four times, preferably at least eight times long as the second lever arm 28.

By a deactivated filled gas cartridge 3, the first lever arm 27 is at maximum distance from the wall of the injector housing 2 and the second, shorter lever arm 28, is positioned on the wall of the injector housing 2. The lever arm can run at an angle of preferably more than 3°, for example 5 to 20°, starting from the tilt axis A, relative to the sensor housing.

For the arrangement of the second L-shaped lever 25, a second lever bearing 29 sticks out from the main cylindrical third injector housing section 23. The second lever bearing 29 is positioned opposite the first lever bearing 17 to an end area 30 of the injector unit 1 that is fixed opposite to the end face 31. Aligned to the first lever mount 17, the second lever mount 29 also has two lugs 35 and 36 and a gap 37, into which the lever 25 can be inserted at least part by part and is pivotably mounted by means of an axle pin 38, arranged in openings in the two lugs 35 and 36. This first lever 25 will be called hereinafter a pivot lever. Through the movement of this lever, a force deviation occurs, of the operating force, from one radial direction opposite to the injection housing 2 in an axial direction, where the force is finally implemented on the gas cartridge 2. Axle bolt 38 defines, in this case, a pivot axis B.

The L-form lever has a first lever arm 39, that should preferably be at least twice as long as the second lever arm 40. At the end of the first lever arm 39, the second lever arm 28 of the first lever 24, holds and presses the first lever arm 39 in a radial direction away from injection housing 2.

The second lever arm 40 is arc-shaped, it grips one end of the gas cartridge 3 that is opposite to the cartridge cap, and exercises axial pressure on the end of the gas cartridge 3 when the first lever arm 39 is operated as described above.

For this purpose, the lever arm 40 has a lug 41 pushing towards the gas cartridge 3 to increase the force and press directly on the end of the gas cartridge through an end opening 42 in the injector housing.

By activating the lever element 16, the force is transferred directly targeting the gas cartridge 3, but only little axial directed force hits the neighboring injection housing 2. By means of the transferred force, the gas cartridge is pressed onto the nozzle 13, and gas pressure is applied onto the syringe piston, which exerts a high pressure on the active ingredient-containing solution by linear movement in channels 12 and 32, to enable penetration under the skin surface.

The presented injection device 1 contains a small number of parts, which can be produced in large quantities. Therefore, the injection device is suitable for single use, aka disposable syringe. Sterilization measures can therefore be spared after using this kind of disposable injection devices.

Apart from the above sealing element, the syringe piston, the nozzle and the gas cartridge, all other parts, especially the injection housing 2 and lever element 6, can be produced from plastic.

For the gas cartridge 3, a CO2 cartridge can be used, such as 12 g one. This gas cartridge is able to release a pressure of 200 Atm around nozzle 13. Through the cross-section reduction 34, the final diameter of the output port 33 area, being in a preferred range of 0.16 to 0.2 mm in comparison to the channel 32 with a diameter of preferably between 2 to 4 mm, it is possible to additionally increase the pressure, preferably by a factor of 10, e.g., to achieve 3000 Atm.

FIG. 4 shows a second production variation of an injection device 51 in accordance with the invention.

This injection device 51 has, like the variation in FIG. 1-3, an injector housing 52 with a cartridge storage chamber 58 and a gas cartridge 53, arranged in a linear and a moveable manner within this cartridge storage chamber 58, that can be activated by a multi-part lever element 63.

The injector housing has an activating insert at the end of the cartridge storage chamber 58 with a pointed, pin-like nozzle 56 for punching the seal of the gas cartridge 53 and with a channel for the transferring of gas into a piston storage chamber 63, in which a piston 60 is mounted in a linear and a moveable manner.

The nozzle 56 is a separate component of the injection device 51, held by an insert holder 57 with a cartridge seal in the remaining injector housing 52.

The cartridge seal will preferably have a cylindrical shape. It is preferably used for linear guidance of the extension situated at the end of the gas cartridge 53.

Like in FIG. 1-3, the injection device 51 also has a combination of two levers 55 and 59, that enable the application of force on the gas cartridge 53, in the same way as the first version.

The syringe piston 60 acts on a sealing attachment 54 that, in this version, is not connected to the syringe piston 60.

The injection device 51 has an administering opening at the end that, as shown for the variation in FIG. 4, is designated, in continuation of a channel, to guide the movement of piston 60 forward and tapers to a point through a cross-sectional reduction.

The gas cartridge 53, e.g., as a CO2 cartridge, can be inserted into the cartridge storage chamber 58 as a replaceable component.

The pneumatically-operated needleless epidermal syringe or syringe can be disinfected, sealed, and delivered filled and ready for use as a so-called single-use application, packed if necessary.

After unpacking the injection device 51, an anti-rotation lock 62 can be deactivated. The anti-rotation lock 62 can be a safety pin, for example, that prevents the lever 55 and the tilt axis A, or the L-shaped lever 59 and the tilt axis B from moving.

After removing this safety pin, the power transmission can follow, by activating of lever 55 onto the gas cartridge 53. Before that, the tip of injection device 51 will be placed on the skin, at the desired point. By a slight finger pressure on lever 55, it can be moved along for a distance of 10-30 mm, preferably 15-20 mm, until it is pushed against the injection housing 52.

This will initiate the linear movement of the gas cartridge 53 in direction of the activation insert's pin, so the gas cartridge can be opened and release the gas through the activation insert's channel and into the syringe piston 10, or onto the sealing element, positioned at the top of the syringe piston 10.

The ratio of the increased force on the gas cartridge 53 can reach more than 10 times, even 13 times, opposite to a direct manual pressure of the two lever arms 55 and 59 and their geometrical design and bearing on the cartridge bottom.

This ensures an easy handling and prevents excessive pressure on the injection spot.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

REFERENCE SYMBOLS

1, 51 Syringe device
2, 52 Injection housing
3, 53 Gas cartridge
4 Cartridge cap
8 seal element
9 Insert
10, 60 Syringe piston
11, 54 seal element
12 channel
13, 56 Nozzle
14 Pin
15 Gas inlet opening
16, 63 Lever element
17 Lever bearing
18 Lug
19 Lug
20 Gap 21 Sensor housing cross-section/Injection housing cross-section
22 Sensor housing cross-section/Injection housing cross-section
23 Sensor housing cross-section/Injection housing cross-section
24. 55 Lever
25, 59 L-form Lever
26 Axle bolt
27 Lever arm
28 Lever arm
29, 61 Lever bearing
30 End section
31 front surface
32 Channel
33 Administering opening
34 Cross-sectional reduction
35 Lug
36 Lug
37 Gap
38 Axle bolt
39 Lever arm
40 Lever arm
41 Lug
42 Opening
57 Insert holder with cartridge seal
58 Cartridge storage chamber
62 Anti-rotation lock/Safety pin
68 Piston storage chamber
A Tilt axis
B Pivot axle
C Housing axle

The invention claimed is:

1. A needleless epidermal syringe configured for needle-free injection of an active ingredient-containing solution onto a subcutaneous tissue, the needleless epidermal syringe comprising:
an injection housing;
a gas cartridge arranged inside the injection housing;
a piston arranged inside the injector housing, wherein the piston is movable through pressure of gas released from the gas cartridge, and wherein due to the pressure from the piston, the active ingredient-containing solution is set free through a discharge opening of the needleless epidermal syringe and is administered to the subcutaneous tissue upon placing the needleless epidermal syringe onto skin; and
a lever element, which when activated, presses the gas cartridge and releases gas onto a nozzle within the injector housing to release the gas in order to move the piston while injecting the active ingredient-containing solution, wherein the nozzle is tapered towards the gas cartridge,
wherein the lever element comprises a first lever and a second lever,
wherein the first lever comprises first and second lever arms,
wherein the second lever arm of the first lever activates the second lever, wherein the first lever of the lever element has a linear shape that is tiltable, as a rocker, around a tilting axis, and
wherein the first lever arm is at least four times as long as the second lever arm.

2. The needleless epidermal syringe of claim 1, wherein the second lever includes first and second lever arms, and wherein the second lever arm of the second lever is mounted in such a way that the second lever arm of the second lever presses on the gas cartridge to release the gas.

3. The needleless epidermal syringe of claim 1, wherein the first and second lever arms of the first lever are situated at such an angle to one another that a force deflection from an activating force occurs in a radial direction to a housing axis of the injection housing into an axially directed force, wherein the force deflection takes place by 80 to 100°.

4. The needleless epidermal syringe of claim 1, wherein the gas cartridge is filled in such a way that the gas cartridge releases a gas pressure of more than 180 ATM onto the piston.

5. The needleless epidermal syringe of claim 1, further comprising:
a channel filled with the active ingredient-containing solution and situated at an end of the discharge opening, wherein a diameter of the discharge opening is ten times smaller than a diameter of the channel.

6. The needleless epidermal syringe of claim 1, wherein the first lever of the lever element is arranged outside the injection housing with a tilt angle of at least 3° relative to the injection housing.

7. The needleless epidermal syringe of claim 1, wherein the second lever of the lever element has an L-shaped shape, and first and second lever arms,
the second lever arm of the first lever acts on the first lever arm of the second lever for axial pressure application to the gas cartridge, and
the first lever arm of the second lever is twice as long as the second lever arm of the second lever.

8. The needleless epidermal syringe of claim 1, wherein the injection housing comprises several parts that can be disconnected from one another, the several parts including a pneumatic drive unit with the gas cartridge, a power transmission unit that moves linearly with the piston, and an active substance chamber with a channel for storing and releasing the active substance-containing solution into the subcutaneous tissue.

9. The needleless epidermal syringe of claim 1, further comprising:
a blocking device, activation of which enables a tilt movement of the lever element.

10. The needleless epidermal syringe of claim 1, wherein the injection housing and the lever element are plastic.

11. The needleless epidermal syringe of claim 1, wherein the lever element transfers, upon activation, direct force onto the gas cartridge.

* * * * *